(12) United States Patent
Alphazan et al.

(10) Patent No.: US 9,579,642 B2
(45) Date of Patent: Feb. 28, 2017

(54) PROCESS FOR THE PREPARATION OF A CATALYST BASED ON TUNGSTEN FOR USE IN HYDROTREATMENT OR IN HYDROCRACKING

(71) Applicant: IFP ENERGIES NOUVELLES, Rueil-Malmaison (FR)

(72) Inventors: Thibault Alphazan, Mions (FR); Audrey Bonduelle, Francheville (FR); Christele Legens, Lyons (FR); Pascal Raybaud, Lyons (FR); Christophe Coperet, Zurich (CH)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 226 days.

(21) Appl. No.: 14/265,655

(22) Filed: Apr. 30, 2014

(65) Prior Publication Data
US 2014/0323779 A1 Oct. 30, 2014

(30) Foreign Application Priority Data

Apr. 30, 2013 (FR) .................... 13 53941

(51) Int. Cl.
| | |
|---|---|
| *B01J 37/08* | (2006.01) |
| *B01J 31/26* | (2006.01) |
| *B01J 37/20* | (2006.01) |
| *B01J 37/02* | (2006.01) |
| *B01J 23/30* | (2006.01) |
| *B01J 31/02* | (2006.01) |
| *B01J 31/22* | (2006.01) |
| *C10G 45/08* | (2006.01) |
| *C10G 47/12* | (2006.01) |
| *B01J 23/888* | (2006.01) |
| *C10G 45/00* | (2006.01) |
| *B01J 35/10* | (2006.01) |
| *B01J 37/00* | (2006.01) |

(52) U.S. Cl.
CPC ............ *B01J 31/26* (2013.01); *B01J 23/30* (2013.01); *B01J 23/888* (2013.01); *B01J 31/0211* (2013.01); *B01J 31/0212* (2013.01); *B01J 31/0228* (2013.01); *B01J 31/2226* (2013.01); *B01J 31/2234* (2013.01); *B01J 37/0203* (2013.01); *B01J 37/0205* (2013.01); *B01J 37/0207* (2013.01); *B01J 37/0213* (2013.01); *B01J 37/20* (2013.01); *C10G 45/00* (2013.01); *C10G 45/08* (2013.01); *C10G 47/12* (2013.01); *B01J 35/10* (2013.01); *B01J 35/1019* (2013.01); *B01J 37/0009* (2013.01); *B01J 2531/64* (2013.01); *B01J 2531/66* (2013.01); *B01J 2531/847* (2013.01); *C07C 2529/072* (2013.01); *C07C 2529/076* (2013.01)

(58) Field of Classification Search
None
See application file for complete search history.

(56) References Cited

U.S. PATENT DOCUMENTS

| | | | | |
|---|---|---|---|---|
| 3,932,308 A | * | 1/1976 | Loveless | B01J 31/0202 502/111 |
| 4,048,109 A | * | 9/1977 | Ryu | B01J 27/10 502/181 |
| 4,085,193 A | * | 4/1978 | Nakajima et al. | B01D 53/9418 423/239.1 |
| 5,137,855 A | * | 8/1992 | Hegedus et al. | B01D 53/8628 502/217 |
| 2011/0250114 A1 | * | 10/2011 | Augustine et al. | B01D 53/8628 423/239.1 |

OTHER PUBLICATIONS

Engweiler, titania based vanadia, chromia and tungsten oxide catalysts prepared by grafting, 1995, p. 97.*

* cited by examiner

*Primary Examiner* — Melvin C Mayes
*Assistant Examiner* — Stefanie Cohen
(74) *Attorney, Agent, or Firm* — Millen White Zelano and Branigan, PC; Csaba Henter; Anthony Zelano

(57) ABSTRACT

The invention concerns a process for the preparation of a catalyst based on tungsten intended for hydrotreatment or hydrocracking processes.
The invention concerns a process for the preparation of a catalyst for carrying out hydrogenation reactions in hydrotreatment and hydrocracking processes. Said catalyst is prepared from at least one mononuclear precursor compound based on tungsten (W), in its monomeric or dimeric form, having at least one W=O or W—OR bond or at least one W=S or W—SR bond where [R=$C_xH_y$ where x≥1 and (x-1)≤y≤(2x+1) or R=Si(OR')$_3$ or R=Si(R')$_3$ where R'=$C_xH_y$, where x'≥1 and (x'-1)≤y'≤(2x'+1)], optionally at least one Mo precursor and optionally at least one promoter element from group VIII. Said precursors are deposited onto an oxide support which is suitable for the process in which it is used, said catalyst advantageously being sulphurized before being deployed in said process.

20 Claims, No Drawings

PROCESS FOR THE PREPARATION OF A CATALYST BASED ON TUNGSTEN FOR USE IN HYDROTREATMENT OR IN HYDROCRACKING

FIELD OF THE INVENTION

The present invention describes a process for the preparation of a catalyst based on tungsten (W) which is particularly effective in the hydrogenation reactions involved in hydrotreatment and hydrocracking processes as well as in the hydrocracking reactions proper involved in hydrocracking processes.

The present invention also relates to the use of said catalyst in hydrotreatment and/or hydrocracking processes.

PRIOR ART

General Remarks on Catalysts for the Hydrotreatment (HDT) and Hydrocracking (HCK) of Hydrocarbon Feeds The composition and use of catalysts for the hydrotreatment and hydrocracking of hydrocarbon feeds have been fully described in the following works respectively: "Catalysis by transition metal sulphides, From Molecular Theory to Industrial Application", 2013, H. Toulhouat, P. Raybaud, and "Hydrocracking Science and Technology", 1996, J. Scherzer, A. J. Gruia, Marcel Dekker Inc.

Thus, catalysts used in refining processes, whether intended for hydrotreatment or hydrocracking reactions, are generally characterized by a hydrodehydrogenating function supplied by the presence of an active phase based on at least one metal from group VIB and optionally at least one metal from group VIII of the periodic classification of the elements. The most common formulations are of the cobalt-molybdenum (CoMo), nickel-molybdenum (NiMo) and nickel-tungsten (NiW) type. These catalysts may be in the bulk form (of specific value for hydrotreatment catalysts) or indeed in the supported state, which in this case employs a porous solid of a different nature. In this latter case, the porous support is generally an amorphous or low crystallinity oxide (alumina, aluminosilicate, etc), optionally associated with a zeolitic or non-zeolitic material. After preparation, at least one metal from group VIB and optionally at least one metal from group VIII constituting said catalysts are often present in an oxidized form. Since the active and stable form for hydrocracking processes (HCK) and hydrotreatment (HDT) processes is the sulphurized form, these catalysts have to undergo a sulphurization step. This may be carried out in a unit associated with the process (referred to as in situ sulphurization) or prior to charging the catalyst into the unit (referred to as ex situ sulphurization).

The skilled person is generally aware that good catalytic performances in the fields of application mentioned above are a function of: 1) the nature of the hydrocarbon feed to be treated; 2) the process employed; 3) the operating conditions for the function which is selected; and 4) the catalyst used. In the latter case, it is also known that a catalyst with a high catalytic potential is characterized by: 1) an optimized hydrodehydrogenating function (associated active phase ideally dispersed at the surface of the support and having a high active phase content) and 2) in the particular case of processes employing HCK reactions, by a good equilibrium between said hydrodehydrogenating function and the cracking function. It should also be noted that ideally, irrespective of the nature of the hydrocarbon feed to be treated, the active sites of the catalyst have to be accessible to the reagents and reaction products while developing a high active surface area, which could lead to specific constraints in terms of structure and texture of the constituent oxide support for said catalysts.

The usual methods leading to the formation of the hydrodehydrogenating phase of the hydrotreatment and hydrocracking catalysts consist of depositing precursor(s) comprising at least one metal from group VIB and optionally at least one metal from group VIII onto an oxide support using a "dry impregnation" technique, followed by steps for maturing, drying and optionally calcining, resulting in the formation of the oxide form of said metal(s) employed. Next comes the final step of sulphurization, generating the active hydrodehydrogenating phase as mentioned above.

The catalytic performances of catalysts obtained from those "conventional" synthesis protocols have been studied extensively. In particular, it has been shown that for relatively high metal contents, phases are formed which are refractory to sulphurization consecutive to the calcining step (sintering phenomenon) (H. Toulhouat, P. Raybaud "Catalysis by transition metal sulphides, From Molecular Theory to Industrial Application", 2013). As an example, in the case of catalysts of the CoMo or NiMo type supported on a support with the nature of alumina, these are 1) crystallites of $MoO_3$, NiO, CoO, $CoMoO_4$ or $Co_3O_4$, of a dimension sufficient to be detected by XRD, and/or 2) species of the type $Al_2(MoO_4)_3$, $CoAl_2O_4$ or $NiAl_2O_4$. The three species cited above, containing the element aluminium, are well known to the skilled person. They result from interaction between the alumina support and the precursor salts in solution of the active hydrodehydrogenating phase, which specifically results in a reaction between the $Al^{3+}$ ions extracted from the alumina matrix and said salts in order to form Anderson heteropolyanions with formula $[Al(OH)_6Mo_6O_{18}]^{3-}$, which are themselves precursors for the phases which are refractory to sulphurization. The presence of this set of species leads to an indirect non-negligible loss of catalytic activity of the associated catalyst as the entirety of the elements belonging to at least one metal from group VIB and optionally at least one metal from group VIII is not used to its maximum potential, since a portion thereof is immobilized in inactive or low activity species.

The catalytic performances of the conventional catalysts described above could thus be improved, in particular by developing novel methods for the preparation of such catalysts which could:
1) ensure good dispersion of the hydrodehydrogenating phase, in particular for high metal contents (for example by controlling the size of the particles based on transition metals, maintaining the properties of these particles after heat treatment before sulphurization, etc.);
2) limiting the formation of species refractory to sulphurization, for example by better control of the interactions between the active hydrodehydrogenating phase (and/or its precursors) and the porous support employed, or by obtaining a better synergy between the transition metals constituting the active phase, etc.;
3) ensuring good diffusion of the reagents and the reaction products while maintaining the high developed active surface areas (optimizing the chemical, textural and structural properties of the porous support).

The NiW pairing is recognized as being the pairing of metals from groups VIB and VIII which is optimal for the hydrogenation of aromatics and also for hydrodenitrogenation, which are key functions in hydrotreatment reactions or for hydrocracking. Despite the large quantities of NiW deposited on the support by the "conventional" route using the usual precursors (ammonium metatungstate and nickel nitrate), and despite the parametric studies concerning the preparation steps, we have not been able to 1) control the dispersion and morphology of the sheets; 2) properly sulphurize the tungsten; and 3) optimize the degree of promotion of the active phase generated on the supports: these are key essentials in substantially reinforcing the hydrogenating power of the active phase and also of carrying out the desired hydrogenation reactions in the hydrotreatment processes and/or in increasing the yield of middle distillates in the hydrocracking process. One of the scientific challenges of recent years has been to optimize the hydrogenating phase deposited on the various supports for catalysts intended for hydrotreatment and hydrocracking.

Thus, it is clearly advantageous to discover means for preparing hydrotreatment catalysts which can be used to obtain novel catalysts with improved performances. The prior art shows that researchers have turned to a variety of methods, including using many and various polyoxometallates, adding doping elements, adding organic molecules with many and various properties (solvation, complexing, etc) or finally, but to a lesser extent because of difficulties in use, using mononuclear precursors.

Preparation of Hydrotreatment and Hydrocracking Catalysts from Polyoxometallates (POM)

The advantage of polyoxometallates has already been mentioned in the prior art. As an example, the document U.S. Pat. No. 2,547,380 mentions the beneficial use of heteropolyacid salts of metals from group VIII such as cobalt or nickel salts of phosphomolybdic acid or silicomolybdic acid. In that patent, the heteropolyacid still contains phosphorus or silicon, this latter element being the central atom of the structure. Such compounds have the disadvantage of producing atomic ratios (element from group VIII/ element from group VI) which are limited. By way of example, cobalt phosphomolybdate has a CoMo ratio of 0.125.

Patent FR 2 749 778 describes the advantage of heteropolyanions with general formula $M_xAB_{12}O_4$, in which M is cobalt or nickel, A is phosphorus, silicon or boron and B is molybdenum or tungsten; x takes the value 2 or more if A is phosphorus, 2.5 or more if A is silicon and 3 or more if A is boron. These structures have the advantage over the structures disclosed in document U.S. Pat. No. 2,547,380 of obtaining atomic ratios (element from group VIII/element from group VI) which are higher and thus produce better performing catalysts. This increase in the ratio is obtained by means of the presence of at least a portion of the molybdenum or tungsten with a valency which is lower than its normal value of six as appears in the composition of phosphomolybdic, phosphotungstic, silicomolybdic or silicotungstic acid, for example.

Patent FR 2 764 211 describes the synthesis and use of heteropolyanions with formula $M_xAB_{11}O_{40}M'C_{(Z-2x)}$ in which M is cobalt or nickel, A is phosphorus, silicon or boron and B is molybdenum or tungsten, M' is cobalt, iron, nickel, copper or zinc, and C is a $H^+$ ion or an alkylammonium cation, x takes the value of 0 to 4.5, z a value between 7 and 9. Thus, this formula corresponds to that claimed in the invention FR 2 749 778, but in which one M' atom is substituted with a B atom. This latter formula has the advantage of producing atomic ratios between the element from group VIII and from group VIB which may be up to 0.5, and thus better promoted active phases.

Patent FR 2 315 721 demonstrates the advantage of using heteropolycompounds with formula $Ni_{x+y/2}AW_{11-y}O_{39-5/2y}$·

$zH_2O$ and more particularly the use of heteropolycompounds with formula $Ni_4SiW_{11}O_{39}$ and formula $Ni_5SiW_9O_{34}$, leading to unexpected catalytic performances during hydrocracking and hydrotreatment.

In all of the cases, by using heteropolymolybdates or heteropolytungstate nickel salts, the teams researched encouraging the metal-promoter interaction by placing them in the same molecular entity, which means that the degree of promotion of the sulphurized catalyst can be controlled and thus the number of active sites can be increased.

Finally, the use of these polyoxometallates trapped in mesostructured silicas has also been revealed in patents FR 2 969 647 and FR 2 969 645. The catalysts of the invention have exhibited highly interesting performances in gas oil hydrotreatment and hydrocracking compared with catalysts prepared in a conventional manner (impregnation of polyoxometallates onto mesoporous supports).

Preparation of Hydrotreatment or Hydrocracking Catalysts by Adding Organic Molecules Adding an organic compound to hydrotreatment catalysts in order to improve their activity is now well known to the skilled person. A number of patents protect the use of various ranges of organic compounds such as mono, di- or poly alcohols which can optionally be etherified (WO 9641848, WO 0176741, U.S. Pat. No. 4,012,340, U.S. Pat. No. 3,954,673, EP 601 722). Catalysts modified with $C_2$-$C_{14}$ monoesters are described in patent applications EP 0 466 568 and EP 1 046 424, but such modifications do not always increase the performance of the catalyst sufficiently for it to comply with specifications concerning the sulphur contents of fuels which are constantly being made more restrictive for the refiners.

In order to overcome this, patent FR 2 880 823 describes the use of a catalyst comprising metals from groups VIB and VIII, a refractory oxide as the support, and an organic compound comprising at least 2 ester carboxylic functions with formula R1-O—CO—R2-CO—O—R1 or R1-CO—O—R2-O—CO—R1, or indeed $C_1$-$C_4$ dialkyl succinate with acetic acid in the patent FR 2 953 740.

Other patents in the prior art describe a gain in activity linked to the combined use of an organic acid or an alcohol on a hydrotreatment catalyst, as described in the patent application published under number JP1995-136523 by KK Japan Energy, or linked to the use of a cyclic oligosaccharide, as in U.S. Pat. No. 2,963,360, for example.

Even though the gains in activity are sometimes poorly explained, the interest in using organic molecules during the preparation of hydrotreatment and hydrocracking catalysts no longer has to be demonstrated, but such preparations are still limited by the number of steps and by the organic molecules to be impregnated being insoluble in the aqueous solutions which are normally used.

Preparation of Hydrotreatment and Hydrocracking Catalysts Using Mononuclear Precursors (Precursor Containing Only One Metal Atom in its Structure)

Preparations concerning supported catalysts starting from different polyoxometallate precursors having only a single molybdenum or tungsten atom in their structure have been known for a long time but are still rare.

In the 1980s, it was shown that the use of organometallic precursors based on Mo or W of the allyl type ($WR_4$ where $R=C_4H_7$) deposited on $SiO_2$ could be used to generate NiW or NiMo catalysts the intrinsic activities of which (activity with respect to Mo or W atom) in hydrodesulphurization were up to 4 times higher than those of catalysts prepared in a more conventional manner (use of ammonium heptamolybdate $(NH_4)_6Mo_7O_{24}$·$6H_2O$ in the case of catalysts prepared from Mo or tungstic acid, $H_2WO_4$ in the case of catalysts prepared from W) (Yermakov et al., Journal of Molecular Catalysis, 1981, 205-214, Yermakov, Journal of Molecular Catalysis, 21, 1983, 35-55 and Yermakov et al., Applied Catalysis 11, 1984, 1-13). Catalysts prepared on silica from organometallic precursors are still more active, however, (activity with respect to Mo or W atom) than catalysts prepared on alumina.

The literature concerning the preparations of the hydrotreatment catalysts from molybdenum is more abundant than that concerning catalysts based on tungsten.

In the 1990s, CoMo on alumina type catalysts were prepared from thiomolybdate (bis(tetrabutylammonium)tetrathiomolybdate $(TBA)_2MoS_4$) salts and the importance of using them was demonstrated for hydrodesulphurization applications (Halbert et al. Journal of Catalysis 130, 1991, 116-129).

In 2008, the advantage of using molybdenum dioxodiacetylacetonate on an organized mesoporous alumina was demonstrated for the preparation of hydrotreatment catalysts (Kaluza et al., Applied Catalysis A: General, 351, 2008, 93-101). These studies then showed that the CoMo and NiMo catalysts prepared from this precursor were more hydrodesulphurizing than commercial catalysts. Patent EP 0 178 711 describes the preparation of hydrotreatment catalysts on silica starting from solutions containing Mo halides, preferably $MoCl_5$, in the presence of nickel and/or cobalt halide, preferably nickel chloride and/or cobalt chloride hexahydrate, $NiCl_2(H_2O)_6$ and $CoCl_2(H_2O)_6$ respectively, in a nitrile type solvent, with optionally a chlorinated solvent in addition.

U.S. Pat. No. 5,137,859 describes the preparation of catalysts used for the hydrodesulphurization of hydrocarbon oil cuts on an alumina support starting from a compound selected from alkoxides or chelating compounds or molybdenum or chromium glycoxides and a compound selected from alkoxides or chelating compounds or nickel or cobalt glycoxides dissolved in an organic solvent selected from alcohols, ethers, ketones and aromatic compounds. The freshly impregnated oxide catalyst then has to undergo a step for drying at a temperature of approximately 150° C. in the presence or absence of oxygen and necessarily a step for calcining at a temperature of at least 200° C. in an atmosphere containing oxygen. Such treatments may encourage denaturing of precursors grafted by calcining the carbon-containing portion and optionally generating polycondensation of the alkoxide species either due to the water present in the heat treatment gas or due to the water which would be liberated during calcining of the carbonaceous groups. Thus, it can be assumed that the dispersion initially supplied during grafting of the intact species is lost and fewer active sites are generated on the surface after sulphurization.

Families of mononuclear precursors based on tungsten used for hydrotreatment applications are more restricted and essentially only involve carbonyl compounds or the use of tungstate salts in their monomeric form ($WO_4^{2-}$).

In 2006, Sanchez et al. (Sanchez et al. Energy and Fuels, 20, 2006, 245-249) thus prepared NiW catalysts from tungstic acid ($H_2WO_4$) dissolved in an aqueous $NH_3$ solution on alumina for paraffin oil dewaxing.

The use of $W(CO)_6$, tungsten carbonyl, to prepare hydrotreatment catalysts has been widely used, with results which are not convincing in terms of control of the preparation and the loading of W atoms (J. L. Bilhou, A. Theolier, A. K. Smith, J. M. Basset, J. Mol. Catal. 3 (19771978) 245, A. Cichowlas, E. P. Yesodharan, A. Brenner, Appl. Catal. 11(1984) 353, D. A. Hucul, A. Brenner, J. Chem. Soc., Chem. Commun. (1982) 830. A. Brenner, D. A. Hucul, J. Catal. 61 (1980) 216. D. A. Hucul, A. Brenner, J. Phys. Chem. 85 (1981) 496. A. Brenner, D. A. Hucul, J. Am. Chem. Soc. 102 (1980) 2484. I. M. Baibich, F. C. Stedile, I. J. R. Baumvol, J. H. Z. dos Santos, V. E. Santarosa, Phys. Stat. Sol. (1995) 519. R. F. Howe, Inorg. Chem. 15 (1976) 486. A. Kazusaka, R. F. Howe, J. Catal. 63 (1980) 447. A. Kazusaka, R. F. Howe, J. Mol. Catal. 9 (1980) 199. A. Zeccina, E. E. Platero, C. O. Arean, Inorg. Chem. 27 (1988) 102. S. Sivasanker, A. V. Ramaswamy, Indian J. Technol. 21 (1983) 339). That precursor was widely employed for the preparation of catalysts with the formulation CoW with results of varying promise, but with a loss of dispersion and activity when the catalyst is highly loaded with tungsten (Suvanto et al., Applied Catalysis A: General 181, 1999, 189-199), the methods for the preparation of catalysts with the formulation CoW by a conventional pathway (POM) do not generally produce very good catalytic performances due to poor promotion. More exotic preparations have been proposed, such as in the article by Vradman et al. (Vradman et al., Journal of Catalysis, 213, 2003, 163-175) where the hydrotreatment catalysts are prepared by impregnating a mesostructured silica with a solution of diphenylmethane in which the $W(CO)_6$ and elemental sulphur have been dissolved.

The Applicant's research has thus led to the preparation of hydrogenation catalysts from tungsten and optionally molybdenum and optionally at least one element from group VIII, in particular nickel, by modifying the chemical and structural composition of the metallic species, precursors of the active phases, in order to modify the interactions between the support and these precursors in order to better sulphurize the tungsten, which is recognized as being difficult to sulphurize, but also in order to modify the interactions between the support and the active sulphide phase of the catalyst in order to disperse it better. In particular, the Applicant's work has led to the use of mononuclear precursors based on tungsten in their monomeric or dimeric form having at least one W=O or W—OR bond or at least one W=S or W—SR bond where [R=$C_xH_y$, where x≥1 and (x-1)≤y≤(2x+1) or R=$Si(OR')_3$ or R=$Si(R')_3$ where R'=$C_{x'}H_{y'}$, where x'≥1 and (x'-1)≤y'≤(2x'+1)], as particular precursors of the active phase of the catalysts used in hydrogenation reactions in hydrotreatment processes and processes for the hydrocracking of hydrocarbon feeds in accordance with the invention.

The Applicant has thus demonstrated that a supported catalyst prepared from at least one mononuclear precursor based on W in its monomeric or dimeric form and having at least one W=O or W—OR bond or at least one W=S or W—SR bond where [R=$C_xH_y$, where x≥1 and (x-1)≤y≤(2x+1) or R=$Si(OR')_3$ or R=$Si(R')_3$ where R'=$C_{x'}H_{y'}$, where x'≥1 and (x'-1)≤y'≤(2x'+1)], exhibits improved sulphurization and improved catalytic activity compared with catalysts prepared from standard precursors such as polyoxometallates, said catalyst having advantageously been pre-sulphurized then used in a hydrotreatment or hydrocracking process.

DESCRIPTION OF THE INVENTION

Aims of the Invention

The invention concerns a process for the preparation of a supported catalyst starting from at least one mononuclear precursor based on tungsten in its monomeric or dimeric form, having at least one W=O or W—OR bond or at least one W=S or W—SR bond where [R=$C_xH_y$, where x≥1 and (x-1)≤y≤(2x+1) or R=Si(OR')$_3$ or R=Si(R')$_3$ where R'=$C_xH_{y'}$, where x'≥1 and (x'-1)≤y'≤(2x'+1)], and optionally a precursor of molybdenum, and optionally at least one element from group VIII.

The invention also concerns the catalyst that can be prepared by said preparation process.

Finally, the invention concerns the use of said catalyst which can be prepared in this manner in hydrogenation reactions, in particular in hydrotreatment and hydrocracking processes.

SUMMARY OF THE INVENTION

The invention concerns a process for the preparation of a catalyst comprising at least one support, optionally at least one metal from group VIII of the periodic classification of the elements and at least tungsten, in which the tungsten is introduced onto the support, in an organic solvent A, in the form of at least one mononuclear precursor compound based on W, in its monomeric or dimeric form, having at least one W=O or W—OR bond or at least one W=S or W—SR bond where [R=$C_xH_y$, where x≥1 and (x-1)≤y≤(2x+1) or R=Si(OR')$_3$ or R=Si(R')$_3$ where R'=$C_xH_{y'}$, where x'≥1 and (x'-1)≤y'≤(2x'+1)].

The metal from group VIII may be selected from cobalt, iron or nickel.

Preferably, the metal from group VIII is nickel.

The tungsten precursor is advantageously a mononuclear precursor based on tungsten W, used in its monomeric or dimeric form, with formula W(=O)$_n$(=S)$_{n'}$(OR)$_a$(SR')$_b$(L1)$_c$(L2)$_d$(L3)$_e$(L4)$_f$(L5)$_g$, where R=$C_xH_y$, where x≥1 and (x-1)≤y≤(2x+1) or R=Si(OR'')$_3$ or R=Si(R'')$_3$ where R''=$C_{x''}H_{y''}$ where [x''≥1 and (x''-1)≤y''≤(2x''+1)], where R'=$C_xH_{y'}$, where x'≥1 and (x'-1)≤y'≤(2x'+1) or R'=Si(OR''')$_3$ or R'=Si(R''')$_3$ where R'''=$C_{x'''}H_{y'''}$ where [x'''≥1 and (x'''-1)≤y'''≤(2x'''+1)], where 0≤n+n'≤2 and 0≤n≤2 and 0≤n'≤2, where, if n=n'=0, then (a≠0 or b≠0) and [(a+b+c+d+e+f+g=6 and 0≤a≤6, 0≤b≤6, 0≤c≤6, 0≤d≤6, 0≤e≤6, 0≤f≤6, 0≤g≤6, or (a+b+c+d+e+f+g=5 and 0≤a≤5, 0≤b≤5, 0≤c≤5, 0≤d≤5, 0≤e≤5, 0≤f≤5, 0≤g≤5), or (a+b+c+d+e+f+g=4 and 0≤a≤4, 0≤b≤4, 0≤c≤4, 0≤d≤4, 0≤e≤4, 0≤f≤4, 0≤g≤4)], where, if [(n=1 and n'=0) or (n'=1 and n=0)], then [a+b+c+d+e+f+g=4 and 0≤a≤4, 0≤b≤4, 0≤c≤4, 0≤d≤4, 0≤e≤4, 0≤f≤4, 0≤g≤4)] or [(a+b+c+d+e+f+g=3 and 0≤a≤3, 0≤b≤3, 0≤c≤3, 0≤d≤3, 0≤e≤3, 0≤f≤3, 0≤g≤3)], where, if [n+n'=2 and 0≤n≤2 and 0≤n'≤2], then (a+b+c+d+e+f+g=2 and 0≤a≤2, 0≤b≤2, 0≤c≤2, 0≤d≤2, 0≤e≤2, 0≤f≤2, 0≤g≤2), with (L1), (L2), (L3), (L4) and (L5) being selected from ligands of the type THF, dimethyl ether, dimethylsulphide, P(CH$_3$)$_3$, allyl, aryl, halogens, amine, acetate, acetylacetonate, halide, hydroxide, —SH or any other ligand known to the skilled person.

Preferably, the precursor is selected from W(OEt)$_5$, W(OEt)$_6$, W(=O)(OEt)$_4$, W(=S)(OEt)$_4$, W(=S)(SEt)$_4$, W(=O)$_2$(OEt)$_2$, W(OC$_6$H$_5$)$_6$, W(SEt)$_5$, W(SEt)$_6$, W(OEt)$_3$(SEt)$_2$, W(OEt)$_4$(SEt), W(=O)(OEt)$_3$(acac) with Et=CH$_2$CH$_3$ (ethyl group) and acac=(CH$_3$COCHCOCH$_3$)$^-$ (acetylacetonate) in their monomeric or dimeric form.

Molybdenum may also be introduced into the catalyst in the form of a precursor in an aqueous, alcoholic or organic solvent.

Advantageously, the molybdenum precursor is a mononuclear precursor, used in its monomeric or dimeric form, comprising at least one Mo=O or Mo—OR bond or at least one Mo=S or Mo—SR bond where [R=$C_xH_y$, where x≥1 and (x-1)≤y≤(2x+1) or R=Si(OR')$_3$ or R=Si(R')$_3$ where R'=$C_xH_{y'}$, where x'≥1 and (x'-1)≤y'≤(2x'+1)].

Preferably, the molybdenum precursor is selected from compounds with formula Mo(=O)$_n$(=S)$_{n'}$(OR)$_a$(SR')$_b$(L1)$_c$(L2)$_d$(L3)$_e$(L4)$_f$(L5)$_g$, where R=$C_xH_y$, where x≥1 and (x-1)≤y≤(2x+1) or R=Si(OR'')$_3$ or R=Si(R'')$_3$ where R''=$C_{x''}H_{y''}$ where [x''≥1 and (x''-1)≤y''≤(2x''+1)], where R'=$C_xH_{y'}$, where x'≥1 and (x'-1)≤y'≤(2x'+1) or R'=Si(OR''')$_3$ or R'=Si(R''')$_3$ where R'''=$C_{x'''}H_{y'''}$ where [x'''≥1 and (x'''-1)≤y'''≤(2x'''+1)], where 0≤n+n'≤2 and 0≤n≤2 and 0≤n'≤2, where, if n=n'=0, then (a≠0 or b≠0) and [(a+b+c+d+e+f+g=6 and 0≤a≤6, 0≤b≤6, 0≤c≤6, 0≤d≤6, 0≤e≤6, 0≤f≤6, 0≤g≤6, or (a+b+c+d+e+f+g=5 and 0≤a≤5, 0≤b≤5, 0≤c≤5, 0≤d≤5, 0≤e≤5, 0≤f≤5, 0≤g≤5), or (a+b+c+d+e+f+g=4 and 0≤a≤4, ≤b≤4, 0≤c≤4, 0≤d≤4, 0≤e≤4, 0≤f≤4, 0≤g≤4)], where, if [(n=1 and n'=0) or (n'=1 and n=0)], then [a+b+c+d+e+f+g=4 and 0≤a≤4, 0≤b≤4, 0≤c≤4, 0≤d≤4, 0≤e≤4, 0≤f≤4, 0≤g≤4)] or [(a+b+c+d+e+f+g=3 and 0≤a≤3, 0≤b≤3, 0≤c≤3, 0≤d≤3, 0≤e≤3, 0≤f≤3, 0≤g≤3)], where, if [n+n'=2 and 0≤n≤2 and 0≤n'≤2], then (a+b+c+d+e+f+g=2 and 0≤a≤2, 0≤b≤2, 0≤c≤2, 0≤d≤2, 0≤e≤2, 0≤f≤2, 0≤g≤2), with (L1), (L2), (L3), (L4) and (L5) being selected from ligands of the type THF, dimethyl ether, dimethylsulphide, P(CH$_3$)$_3$, allyl, aryl, halogens, amine, acetate, acetylacetonate, halide, hydroxide, —SH, or any other ligand known to the skilled person.

Highly preferably, the molybdenum precursor is Mo(OEt)$_5$.

The tungsten, optionally the molybdenum, optionally the metal or metals from group VIII, may be introduced simultaneously or successively.

The preparation process may comprise at least one final step for gas phase sulphurization carried out in situ and/or ex situ.

More particularly, the preparation process may comprise at least the following steps:
 a) impregnation by bringing a solution S comprising the organic solvent A with at least said mononuclear precursor based on tungsten, in its monomeric or dimeric form, having at least one W=O or W—OR bond or at least one W=S or W—SR bond where [R=$C_xH_y$, where x≥1 and (x-1)≤y≤(2x+1) or R=Si(OR')$_3$ or R=Si(R')$_3$ where R'=$C_xH_{y'}$, where x'≥1 and (x'-1)≤y'≤(2x'+1)], into contact with a porous mineral support, which has been calcined under low vacuum or high vacuum or in a stream of inert gas;
 b) maturing in an anhydrous atmosphere;
 c) drying the impregnated support in an anhydrous atmosphere or under low vacuum or high vacuum or in a stream of inert gas;
 d) ex situ sulphurization in a H$_2$S/H$_2$ or H$_2$S/N$_2$ mixture containing at least 5% by volume of H$_2$S in the mixture at a temperature equal to or higher than ambient temperature.

The optional molybdenum precursor may be introduced into the impregnation step a) in the same solution S as the tungsten precursor.

The optional molybdenum precursor may be introduced in a post-impregnation step a2) after drying c).

The optional metal from group VIII may be introduced into step a) in the same solution S as the tungsten precursor or after the drying c) in a post-impregnation step a2) with the aid of a solution using an organic solvent B, or after the sulphurization step d) in a post-impregnation step a3) with the aid of an aqueous or organic solution.

The invention also concerns a catalyst which is susceptible of being prepared in accordance with said process.

Said catalyst may comprise a cumulative quantity of (tungsten+molybdenum) in the range 4% to 30% by weight and a metal or metals from group VIII content in the range 0.1% to 8% by weight with respect to the total catalyst weight.

The invention also concerns the use of said catalyst in reactions for the hydrogenation of hydrocarbon feeds, preferably for hydrotreatment or hydrocracking.

DETAILED DESCRIPTION OF THE INVENTION

The invention concerns a process for the preparation of a supported catalyst starting from at least one mononuclear precursor based on tungsten, in its monomeric or dimeric form, having at least one W=O or W—OR bond or at least one W=S or W—SR bond where [R=$C_xH_y$ where x≥1 and (x−1)≤y≤(2x+1) or R=Si(OR')$_3$ or R=Si(R')$_3$ where R'=$C_{x'}H_{y'}$ where x'≥1 and (x'−1)≤y'≤(2x'+1)], and optionally a precursor of molybdenum, and optionally at least one element from group VIII.

Said precursors are deposited, using any method known to the skilled person, onto an oxide support suitable for the process in which it is used, said catalyst advantageously being sulphurized before being deployed in said process.

One of the advantages of the present invention thus resides in an innovative preparation of hydrotreatment catalysts based on tungsten which allows for better dispersion by grafting of the precursors onto the support surface, even onto a silica support, and by better sulphurization of tungsten, recognized as being a species which is difficult to sulphurize. These improvements mean that potentially, more active phase of the sulphide type can be generated, and thus potentially, more active sites can be generated for carrying out the desired hydrogenation or hydrocracking reactions and thus higher activities for the catalysts of the invention can be generated compared with those encountered in the literature, or activities can be generated which are identical to conventional catalysts but with half the number of metal atoms on the catalyst.

Preferably, said preparation process comprises at least the following steps:
a) a step for impregnation by bringing a solution comprising an organic solvent A and at least one mononuclear precursor based on W, in its monomeric or dimeric form, having at least one W=O or W—OR bond or at least one W=S or W—SR bond where [R=$C_xH_y$ where x≥1 and (x−1)≤y≤(2x+1) or R=Si(OR')$_3$ or R=Si(R')$_3$ where R'=$C_{x'}H_{y'}$ where x'≥1 and (x'−1)≤y'≤(2x'+1)], into contact with a porous mineral support, which has advantageously been calcined under low vacuum or high vacuum or in a stream of inert gas to evacuate the water which might be physisorbed on said support;
b) a maturation step;
c) a step for drying the impregnated support, advantageously carried out at a temperature not exceeding 200° C., in an anhydrous atmosphere or under low vacuum or high vacuum or in a stream of inert gas;
d) a step for sulphurization, preferably carried out ex situ in a $H_2S/H_2$ or $H_2S/N_2$ mixture containing at least 5% by volume of $H_2S$ in the mixture at a temperature equal to or higher than ambient temperature.

The optional element or elements from group VIII, hereinafter denoted the promoter(s), may be introduced in solution either:
i) at the impregnation step a), co-impregnated with the mononuclear precursor based on tungsten;
ii) after the drying step c) in a step known as post-impregnation a2) with the aid of a solution using an organic solvent B. In this case, a second step for maturation b2) and a second drying step c2) are necessary and may be carried out under the same conditions as the conditions described during steps b) and c);
iii) after step d), in a post-impregnation step a3) with the aid of an aqueous solution or an organic solution. In this case, it is necessary to add a new maturation step b3), a new drying step c3) and a new sulphurization step d2) before using the catalyst in the hydrotreatment or hydrocracking process in accordance with the invention.

The mononuclear precursor based on tungsten (W), used in its monomeric or dimeric form, in accordance with the invention advantageously has the formula W(=O)$_n$(=S)$_{n'}$(OR)$_a$(SR')$_b$(L1)$_c$(L2)$_d$(L3)$_e$(L4)$_f$(L5)$_g$,
where R=$C_xH_y$ where x≥1 and (x−1)≤y≤(2x+1) or R=Si(OR'')$_3$ or R=Si(R'')$_3$ where R''=$C_{x''}H_{y''}$ where [x''≥1 and (x''−1)≤y''≤(2x''+1)],
where R'=$C_{x'}H_{y'}$ where x'≥1 and (x'−1)≤y'≤(2x'+1) or R'=Si(OR''')$_3$ or R'=Si(R''')$_3$ where R'''=$C_{x'''}H_{y'''}$ where [x'''≥1 and (x'''−1)≤y'''≤(2x'''+1)],
where 0≤n+n'≤2 and 0≤n≤2 and 0≤n'≤2,
where, if n=n'=0, then (a≠0 or b≠0) and [(a+b+c+d+e+f+g=6 and 0≤a≤6, 0≤b≤6, 0≤c≤6, 0≤d≤6, 0≤e≤6, 0≤f≤6, 0≤g≤6, or (a+b+c+d+e+f+g=5 and 0≤a≤5, 0≤b≤5, 0≤c≤5, 0≤d≤5, 0≤e≤5, 0≤f≤5, 0≤g≤5), or (a+b+c+d+e+f+g=4 and 0≤a≤4, 0≤b≤4, 0≤c≤4, 0≤d≤4, 0≤e≤4, 0≤f≤4, 0≤g≤4)],
where, if [(n=1 and n'=0) or (n'=1 and n=0)], then [(a+b+c+d+e+f+g=4 and 0≤a≤4, 0≤b≤4, 0≤c≤4, 0≤d≤4, 0≤e≤4, 0≤f≤4, 0≤g≤4)] or [(a+b+c+d+e+f+g=3 and 0≤a≤3, ≤b≤3, 0≤c≤3, 0≤d≤3, 0≤e≤3, 0≤f≤3, 0≤g≤3)],
where, if [n+n'=2 and 0≤n≤2 and 0≤n'≤2], then (a+b+c+d+e+f+g=2 and 0≤a≤2, 0≤b≤2, 0≤c≤2, 0≤d≤2, 0≤e≤2, 0≤f≤2, 0≤g≤2),
with (L1), (L2), (L3), (L4) and (L5) being ligands which are well known to the skilled person and of type THF, dimethyl ether, dimethylsulphide, P(CH$_3$)$_3$, allyl, aryl, halogens (selected from fluorine, chlorine and bromine), amine, acetate, acetylacetonate, halide, hydroxide, —SH, ETC. Preferably, the ligands are selected from acetylacetonate, THF and dimethyl ether.

Preferably, the precursors in accordance with the invention do not contain the ligand (L1), (L2), (L3), (L4) and (L5).

Preferably, the precursors in accordance with the invention are W(OEt)$_5$, W(OEt)$_6$, W(=O)(OEt)$_4$, W(=S)(OEt)$_4$, W(=S)(SEt)$_4$, W(=O)$_2$(OEt)$_2$, W(OC$_6$H$_5$)$_6$, W(SEt)$_5$, W(SEt)$_6$, W(OEt)$_4$(SEt), W(OEt)$_3$(SEt)$_2$, W(OEt)$_2$(SEt)$_3$, W(OEt)(SEt)$_4$, W(=O)(OEt)$_3$(acac) with Et=CH$_2$CH$_3$ (ethyl group) and acac=(CH$_3$COCHCOCH$_3$)$^-$ (acetylacetonate), in their monomeric or dimeric form.

Highly preferably, the precursors in accordance with the invention are W(OEt)$_5$ or W(OEt)$_6$.

The tungsten content (W) is generally in the range 4% to 30% by weight with respect to the final catalyst, and preferably in the range 7% to 25% by weight with respect to the final catalyst, obtained after the last preparation step, before deploying it in the hydrotreatment process or the hydrocracking process.

The surface density, which corresponds to the quantity of tungsten atoms W deposited per unit surface area of the support, is advantageously in the range 0.5 to 8 atoms of W per square nanometer of support, preferably in the range 1 to 7 W atoms per square nanometer of support.

Step a), for bringing the solution and the support into contact, is an impregnation. Impregnations are well known to the skilled person. The impregnation method of the invention is selected from dry impregnation, excess impregnation, and successive impregnations. The method termed dry impregnation is advantageously used.

The organic solvent A used in step a) is generally an alkane, an alcohol, an ether, a ketone, a chlorinated solvent or an aromatic compound. Cyclohexane and n-hexane are preferably used.

Step b) is a maturation step intended to allow the species to diffuse to the core of the support. It is advantageously carried out in an anhydrous atmosphere (without water), preferably for 30 minutes to 24 hours at ambient temperature. The atmosphere should preferably be anhydrous so as not to polycondense the pre-impregnated precursors.

Drying carried out during step c) is intended to remove the impregnation solvent A. The atmosphere should preferably be anhydrous (no water) so that said pre-impregnated precursors are not polycondensed. Advantageously, the temperature should not exceed 200° C. in order to keep said precursors grafted or deposited on the surface intact. Preferably, the temperature will not exceed 120° C. Highly preferably, drying is carried out under vacuum at ambient temperature. This step can alternatively be carried out by passing through an inert gas.

Sulphurization step d) is advantageously carried out ex situ using a $H_2S/H_2$ or $H_2S/N_2$ gas mixture containing at least 5% by volume of $H_2S$ in the mixture at a temperature which is ambient temperature or higher, at a total pressure equal to or higher than 1 bar for at least 2 h. Preferably, the sulphurization temperature is 250° C. Highly preferably, the sulphurization temperature is 350° C.

Sulphurization step d) may also [or in addition to step d) carried out ex situ] be carried out in situ at the start of carrying out the catalytic process using the catalyst, for example a hydrotreatment or hydrocracking process, using any sulphurization process which is well known to the skilled person, as described above.

The preferred elements from group VIII are non-noble elements: they are selected from Ni, Co and Fe. Preferably, the element from group VIII is nickel. The metal from group VIII is advantageously introduced in the form of salts, chelating compounds, alkoxides or glycoxides, and preferably in the form of acetylacetonate or acetate.

If the promoter is introduced as described in the invention in i) and ii), the compounds containing the element from group VIII are preferably sulphur-containing compounds, oxygen-containing compounds, chelating compounds, alkoxides and glycoxides. Preferably, it is introduced in the form of acetylacetonate or acetate.

If the promoter is introduced as described in the invention at iii), the compounds containing the element from group VIII may be introduced in the form of salts, sulphur-containing compounds, oxygen-containing compounds, chelating compounds, alkoxides and glycoxides. Preferably, it is introduced in the form of acetylacetonate or acetate.

The sources of elements from group VIII which may advantageously be used in the form of salts are well known to the skilled person. They are selected from nitrates, sulphates, hydroxides, phosphates, halides selected from chlorides, bromides and fluorides.

The promoter elements from group VIII are advantageously present in the catalyst in quantities in the range 0.1% to 8% by weight, preferably in the range 0.5% to 5% by weight with respect to the final catalyst obtained after the last preparation step, before using it in the hydrotreatment process or the hydrocracking process.

The organic solvent B used when the promoter is introduced after step c) in a step termed post-impregnation is generally an alkane, an alcohol, an ether, a ketone, a chlorinated compound or an aromatic compound. Toluene, benzene, dichloromethane, tetrahydrofuran, cyclohexane, n-hexane, ethanol, methanol and acetone are preferably used.

The solvent used for impregnation of the promoter (element from group VIII) in the case of step iii) corresponds either to the organic solvent B in the case in which non-saline precursors and water are used, or an alcohol when the precursors are saline.

The hydrodehydrogenating function of the catalyst of the invention is ensured by at least one element from group VIB which is tungsten, W, and optionally molybdenum, Mo, and optionally by at least one element from group VIII. Advantageously, the hydrodehydrogenating function is selected from the group formed by combinations of the elements, nickel-tungsten or nickel-tungsten-molybdenum. In the case in which high hydrodesulphurization activity is required in addition to hydrogenation reactions, the hydrodehydrogenating function is advantageously ensured by an association of nickel and tungsten in the presence of molybdenum.

In a particular embodiment, the precursor based on molybdenum Mo may also be a mononuclear precursor, used in its monomeric or dimeric form, comprising at least one Mo=O or Mo—OR bond or at least one Mo=S or Mo—SR bond where [R=$C_xH_y$ where x≥1 and (x−1)≤y≤5 (2x+1) or R=$Si(OR')_3$ or R=$Si(R')_3$ where R'=$C_xH_{y'}$ where x'≥1 and (x'−1)≤y'≤(2x'+1)].

In a first variation, the mononuclear precursor based on molybdenum Mo may be introduced to step a) in the same solution as that containing at least one precursor based on W. The mononuclear precursor based on Mo, used in its monomeric or dimeric form, advantageously has the formula $Mo(=O)_n(=S)_{n'}(OR)_a(SR')_b(L1)_c(L2)_d(L3)_e(L4)_f(L5)_g$,
where R=$C_xH_y$ where x≥1 and (x−1)≤y≤(2x+1) or R=$Si(OR'')_3$ or R=$Si(R'')_3$ where R''=$C_{x'}H_{y'}'$ where [x''≥1 and (x''−1)≤y''≤(2x''+1)],
where R'=$C_xH_{y'}$ where x'≥1 and (x'−1)≤y'≤(2x'+1) or R'=$Si(OR''')_3$ or R'=$Si(R''')_3$ where R'''=$C_{x'''}H_{y'''}$ where [x'''≥1 and (x'''−1)≤y'''≤(2x'''+1)],
where 0≤n+n'≤2 and 0≤n≤2 and 0≤n'≤2,
where, if n=n'=0, then (a≠0 or b≠0) and [(a+b+c+d+e+f+g=6 and 0≤a≤6, 0≤b≤6, 0≤c≤6, 0≤d≤6, 0≤e≤6, 0≤f≤6, 0≤g≤6, or (a+b+c+d+e+f+g=5 and 0≤a≤5, 0≤b≤5, 0≤c≤5, 0≤d≤5, 0≤e≤5, 0≤f≤5, 0≤g≤5), or (a+b+c+d+e+f+g=4 and 0≤a≤4, 0≤b≤4, 0≤c≤4, 0≤d≤4, 0≤e≤4, 0≤f≤4, 0≤g≤4)],
where, if [(n=1 and n'=0) or (n'=1 and n=0)], then [a+b+c+d+e+f+g=4 and 0≤a≤4, 0≤b≤4, 0≤c≤4, 0≤d≤4, 0≤e≤4, 0≤f≤4, 0≤g≤4) or [(a+b+c+d+e+f+g=3 and 0≤a≤3, 0≤b≤3, 0≤c≤3, 0≤d≤3, 0≤e≤3, 0≤f≤3, 0≤g≤3)],
where, if [n+n'=2 and 0≤n≤2 and 0≤n'≤2], then (a+b+c+d+e+f+g=2 and 0≤a≤2, 0≤b≤2, 0≤c≤2, 0≤d≤2, 0≤e≤2, 0≤f≤2, 0≤g≤2),
with (L1), (L2), (L3), (L4) and (L5) being ligands which are well known to the skilled person and of the type THF, dimethyl ether, dimethylsulphide, $P(CH_3)_3$, allyl, aryl, halogens (selected from fluorine, chlorine, bromine), amine, acetate, acetylacetonate, halide, hydroxide, —SH, etc. Preferably, the ligands are selected from acetylacetonate, THF and dimethyl ether.

Preferably, the precursors in accordance with the invention do not contain the ligand (L1), (L2), (L3), (L4) and (L5).

Highly preferably, the molybdenum precursor in accordance with the invention is $Mo(OEt)_5$.

In a second variation, the mononuclear precursor based on molybdenum Mo may be introduced after step c) in a step known as post-impregnation a2) using a solution comprising the molybdenum precursor, Mo, and a solvent selected from alkanes, alcohols, ethers, ketones or aromatic compounds. Preferably, cyclohexane, n-hexane and ethanol are used.

The mononuclear precursor based on Mo, used in its monomeric or dimeric form, in accordance with the invention advantageously has the formula $Mo(=O)_n(=S)_{n'}(OR)_a(SR')_b(L1)_c(L2)_d(L3)_e(L4)_f(L5)_g$, where $R=C_xH_y$ where $x \geq 1$ and $(x-1) \leq y \leq (2x+1)$ or $R=Si(OR'')_3$ or $R=Si(R'')_3$ where $R''=C_{x'}H_{y'}$ where $[x'' \geq 1$ and $(x''-1) \leq y'' \leq (2x''+1)]$, where $R'=C_{x'}H_{y'}$ where $x' \geq 1$ and $(x'-1) \leq y' \leq (2x'+1)$ or $R'=Si(OR''')_3$ or $R'=Si(R''')_3$ where $R'''=C_{x'''}H_{y'''}$ where $[x''' \geq 1$ and $(x'''-1) \leq y''' \leq (2x'''+1)]$, where $0 \leq n+n' \leq 2$ and $0 \leq n \leq 2$ and $0 \leq n' \leq 2$, where, if $n=n'=0$, then $(a \neq 0$ or $b \neq 0)$ and $[(a+b+c+d+e+f+g=6$ and $0 \leq a \leq 6, 0 \leq b \leq 6, 0 \leq c \leq 6, 0 \leq d \leq 6, 0 \leq e \leq 6, 0 \leq f \leq 6, 0 \leq g \leq 6,$ or $(a+b+c+d+e+f+g=5$ and $0 \leq a \leq 5, 0 \leq b \leq 5, 0 \leq c \leq 5, 0 \leq d \leq 5, 0 \leq e \leq 5, 0 \leq f \leq 5, 0 \leq g \leq 5)$, or $(a+b+c+d+e+f+g=4$ and $0 \leq a \leq 4, 0 \leq b \leq 4, 0 \leq c \leq 4, 0 \leq d \leq 4, 0 \leq e \leq 4, 0 \leq f \leq 4, 0 \leq g \leq 4)]$, where, if $[(n=1$ and $n'=0)$ or $(n'=1$ and $n=0)]$, then $[a+b+c+d+e+f+g=4$ and $0 \leq a \leq 4, 0 \leq b \leq 4, 0 \leq c \leq 4, 0 \leq d \leq 4, 0 \leq e \leq 4, 0 \leq f \leq 4, 0 \leq g \leq 4)]$ or $[(a+b+c+d+e+f+g=3$ and $0 \leq a \leq 3, 0 \leq b \leq 3, 0 \leq c \leq 3, 0 \leq d \leq 3, 0 \leq e \leq 3, 0 \leq f \leq 3, 0 \leq g \leq 3)]$, where, if $[n+n'=2$ and $0 \leq n \leq 2$ and $0 \leq n' \leq 2]$, then $(a+b+c+d+e+f+g=2$ and $0 \leq a \leq 2, 0 \leq b \leq 2, 0 \leq c \leq 2, 0 \leq d \leq 2, 0 \leq e \leq 2, 0 \leq f \leq 2, 0 \leq g \leq 2)$, with (L1), (L2), (L3), (L4) and (L5) being ligands which are well known to the skilled person and of the type THF, dimethyl ether, dimethylsulphide, $P(CH_3)_3$, allyl, aryl, halogens (selected from fluorine, chlorine, bromine) amine, acetate, acetylacetonate, halide, hydroxide, —SH, etc. Preferably, the ligands are selected from acetylacetonate, THF and dimethyl ether.

Preferably, the precursors in accordance with the invention do not contain the ligand (L1), (L2), (L3), (L4) and (L5).

Highly preferably, the molybdenum precursor in accordance with the invention is $Mo(OEt)_5$.

In this case, the quantity of tungsten, W, added to the quantity of molybdenum, Mo, is in the range 4% to 30% by weight with respect to the final catalyst, preferably in the range 7% to 25% by weight with respect to the final catalyst, obtained after the last preparation step, before being used in the hydrotreatment process or the hydrocracking process.

In this particular case, the elements from group VIB deposited on the catalyst are constituted by between 1% and 100% of W, preferably between 33% and 100% of W, more preferably between 75% and 100% of W; still more preferably, the single element from group VIB present on the catalyst is W.

The support for the catalyst of the invention is a porous mineral support which advantageously comprises at least aluminium and/or at least silicon.

Preferably, said support comprises at least one aluminium oxide or at least one silicon oxide. Advantageously, said support may or may not be acidic. Advantageously, said support may or may not be mesostructured.

Said porous mineral support may advantageously be selected from transition aluminas, doped aluminas, preferably with phosphorus, boron and/or fluorine, silicalite and silicas, aluminosilicates, preferably amorphous or of low crystallinity, crystallized non-zeolitic molecular sieves such as silicoaluminophosphates, aluminophosphates, ferrosilicates, titanium silicoaluminates, borosilicates, chromosilicates and transition metal aluminophosphates, alone or as a mixture.

In the case in which said porous mineral support is selected from transition aluminas, silicalite and silicas such as mesoporous silicas, for example, said support is not acidic. The term "transition alumina" means, for example, an alpha phase alumina, a delta phase alumina, a gamma phase alumina or a mixture of aluminas from these various phases.

In the case in which said porous mineral support is selected from aluminosilicates, preferably amorphous or of low crystallinity, non-zeolitic crystallized molecular sieves such as silicoaluminophosphates, aluminophosphates, ferrosilicates, titanium silicoaluminates, borosilicates, chromosilicates and transition metal aluminophosphates, doped aluminas, preferably with phosphorus, boron and/or fluorine, said support is acidic. Any known silica-alumina or any aluminosilicate known to the skilled person is suitable in the context of the invention.

When said porous mineral support is said to be mesostructured, it then comprises elementary particles organized on the mesopore scale of the material of the invention, i.e. an organized porosity on the scale of pores with a uniform diameter in the range 1.5 to 50 nm, preferably in the range 1.5 to 30 nm and still more preferably in the range 4 to 20 nm and distributed in a homogeneous and regular manner in each of said particles (mesostructuring). The material located between the mesopores of the elementary mesostructured particle is amorphous and forms walls or partitions the thickness of which is in the range 1 to 30 nm, preferably in the range 1 to 10 nm. The thickness of the walls corresponds to the distance separating a first mesopore from a second mesopore, the second mesopore being the pore closest to said first mesopore. The organization of the mesoporosity described above leads to a structure of said constituent particle of said support, which may be hexagonal, vermicular or cubic, preferably hexagonal. Preferably, said mesostructured porous mineral support is selected from silica and silica-alumina.

In addition to at least one of the oxide compounds cited above, the porous mineral support of the invention, whether or not it is acidic, mesostructured or not mesostructured, may also advantageously comprise at least one zeolite and in particular but not restricted to those listed in the "Atlas of Zeolite Framework types", 6$^{th}$ revised edition, 2007, Ch. Baerlocher, L. B. L. McCusker, D. H. Olson". The zeolitic crystals may be selected from the zeolites IZM-2, ZSM-5, ZSM-12, ZSM-48, ZSM-22, ZSM-23, ZBM-30, EU-2, EU-11, Silicalite, Beta, zeolite A, Faujasite, Y, USY, VUSY, SDUSY, Mordenite, NU-10, NU-87, NU-88, NU-86, NU-85, IM-5, IM-12, IM-16, Ferrierite and EU-1. Highly preferably, the zeolitic crystals may be selected from zeolites with structure type MFI, BEA, FAU, and LTA. Different zeolitic crystals and in particular zeolites with a different structure type may be present in the porous mineral support constituting the material in accordance with the invention. In particular, the porous mineral support in accordance with the invention may advantageously comprise at least first zeolitic crystals the zeolite of which is selected from the zeolites IZM-2, ZSM-5, ZSM-12, ZSM-48, ZSM-22, ZSM-23, ZBM-30, EU-2, EU-11, Silicalite, Beta, zeolite A, Faujasite, Y, USY, VUSY, SDUSY, Mordenite, NU-10, NU-87, NU-88, NU-86, NU-85, IM-5, IM-12, IM-16, Ferrierite and EU-1, preferably from zeolites with structure type MFI, BEA, FAU, and LTA and at least second zeolitic crystals the zeolite of which is different from the first zeolitic crystals and is selected from the zeolites IZM-2, ZSM-5, ZSM-12, ZSM-48, ZSM-22, ZSM-23, ZBM-30, EU-2, EU-11, Silicalite, Beta, zeolite A, Faujasite, Y, USY, VUSY, SDUSY, Mordenite, NU-10, NU-87, NU-88, NU-86, NU-85, IM-5, IM-12, IM-16, Ferrierite and EU-1, preferably from zeolites with structure type MFI, BEA, FAU, and LTA. The zeolitic crystals advantageously comprise at least one zeolite which is either entirely silicic or, in addition to silicon, contains at least one element T selected from aluminium, iron, boron, indium, gallium and germanium, preferably aluminium.

In addition to at least one of the oxide compounds cited above, the porous mineral support may also advantageously comprise at least one simple synthetic or natural clay of the dioctahedral 2:1 phyllo silicate or trioctahedral 3:1 phyllo-silicate type such as kaolinite, antigorite, chrysotile, mont-morillonnite, beidellite, vermiculite, talc, hectorite, saponite or laponite. These clays may also optionally have been delaminated.

Preferably, said porous mineral support is selected from mesoporous alumina and silica-alumina used alone or as a mixture, or mesostructured silicas and silica-aluminas, used alone or as a mixture.

The catalyst may be used in any of the forms known to the skilled person: it may be in the form of a powder, in the form of beads or in the form of cylindrical, trilobal or quadrilobal extrudates. Different shapes may be mixed.

In accordance with the invention, said catalyst is advantageously partially sulphurized by means of at least one step for sulphurization in the gas phase described in step d) of the preparation process, before being used in the hydrotreatment or hydrocracking process of the invention. This sulphurization step described in step d) generates the active sulphide phase in a partial manner, but it can be used to prevent leaching of the metallic precursors in contact with the hydrocarbon feed to be treated or possibly in contact with the sulphurization feed. The catalyst obtained is used in a hydrotreatment or hydrocracking unit where it can undergo in situ sulphurization carried out with the aid of the feed to be treated in the presence of hydrogen and hydrogen sulphide ($H_2S$) introduced as is or obtained from the decomposition of an organic sulphur-containing compound selected from dimethyldisulphide (DMDS), dimethylsulphide, n-butylmercaptan and polysulphide compounds. This sulphurization is carried out at a temperature in the range 200° C. to 600° C., preferably in the range 300° C. to 400° C., using processes which are well known to the skilled person.

The Hydrotreatment and Hydrocracking Processes, as Well as Feeds

Finally the invention also concerns the use of the catalyst of the invention in processes for the hydrotreatment and hydrocracking of oil cuts.

The catalyst prepared with the process of the invention may advantageously be used in any process known to the skilled person necessitating hydrocarbon cut hydrogenation reactions, preferably of catalytically cracked gasoline cuts. The hydrotreatment and hydrocracking processes of the invention may advantageously be carried out in any type of reactor operated in fixed bed or moving bed or ebullated bed mode. Preferably, said hydrotreatment process or said hydrocracking process is carried out in a reactor operated in fixed bed mode.

The catalysts obtained by the preparation process of the invention are advantageously used for reactions for the hydrotreatment of hydrocarbon feeds such as oil cuts, cuts obtained from coal or hydrocarbons produced from natural gas, more particularly necessitating hydrogenation reactions: the hydrogenation of aromatics, hydrodenitrogenation, hydrodesulphurization, hydrodemetallization or hydrocracking of hydrocarbon feeds are reactions which may be cited.

These catalysts may also advantageously be used during pre-treatment of catalytically cracked feeds or feeds for the hydrodesulphurization of residues or for the intense hydrodesulphurization of gas oils (ULSD or Ultra Low Sulphur Diesel).

Examples of feeds employed in the hydrotreatment processes are gasolines, gas oils, vacuum gas oils, atmospheric residues, vacuum residues, atmospheric distillates, vacuum distillates, heavy fuels, oils, waxes and paraffins, spent oils, residues or deasphalted crudes, or feeds deriving from thermal or catalytic conversion processes, used alone or as mixtures. The feeds which are treated, in particular those cited above, generally contain heteroatoms such as sulphur, oxygen and nitrogen and, for the heavy feeds, they usually also contain metals.

The operating conditions used in the processes using the reactions for the hydrotreatment of hydrocarbon feeds described above are generally as follows: the temperature is advantageously in the range 180° C. to 450° C., preferably in the range 250° C. to 440° C., the pressure is advantageously in the range 0.5 to 30 MPa, preferably in the range 1 to 18 MPa, the hourly space velocity is advantageously in the range 0.1 to 20 $h^{-1}$, preferably in the range 0.2 to 5 $h^{-1}$, and the hydrogen/feed ratio, expressed as the volume of hydrogen measured under normal temperature and pressure conditions per volume of liquid feed, is advantageously in the range 50 L/L to 2000 L/L.

Examples of the feeds employed in the hydrocracking reactions are LCO (light cycle oil (light gas oils obtained from a catalytic cracking unit)), atmospheric distillates, vacuum distillates, for example gas oils obtained from straight run distillation of crude or conversion units such as FCC, coking or visbreaking units, feeds deriving from aromatics extraction units, lubricating base oils or bases obtained from solvent dewaxing of lubricating base oils, distillates deriving from fixed bed or ebullated bed desulphurization or hydroconversion processes, atmospheric residues and/or vacuum residues and/or deasphalted oils, or the feed may be a deasphalted oil or comprise vegetable oils, or indeed derive from the conversion of feeds obtained from biomass. Said hydrocarbon feed treated in the hydroconversion process of the invention may also be a mixture of said feeds as cited above. The hydrocarbon feeds present in said feed are aromatic compounds, olefinic compounds, naphthenic compounds and/or paraffinic compounds.

Said hydrocarbon feed advantageously comprises heteroatoms. Preferably, said heteroatoms are selected from nitrogen, sulphur and a mixture of these two elements. When nitrogen is present in said feed to be treated, the nitrogen content is 500 ppm or more, and preferably it is in the range 500 to 10000 ppm by weight, more preferably in the range 700 to 4000 ppm by weight and still more preferably in the range 1000 to 4000 ppm. When sulphur is present in said feed to be treated, the sulphur content is in the range 0.01% to 5% by weight, preferably in the range 0.2% to 4% by weight and still more preferably in the range 0.5% to 3% by weight.

Said hydrocarbon feed may optionally advantageously contain metals, in particular nickel and vanadium. The cumulative nickel and vanadium content of said hydrocarbon feed treated using the hydrocracking process of the invention is preferably less than 1 ppm by weight. The asphaltenes content of said hydrocarbon feed is generally less than 3000 ppm, preferably less than 1000 ppm, still more preferably less than 200 ppm.

The hydrocracking process of the invention covers the fields of pressure and conversion from mild hydrocracking to high pressure hydrocracking. The term "mild hydrocracking" means hydrocracking leading to moderate conversions, generally less than 40%, and operating at low pressure, generally between 2 MPa and 10 MPa. The hydrocracking process of the invention is carried out in the presence of at least one hydrotreatment catalyst or hydrocracking catalyst in accordance with the invention. The hydrocracking process of the invention may be carried out in one or two steps, independently of the pressure at which said process is carried out. It is carried out in the presence of one or more catalyst(s) obtained using the preparation process described above, in one or more reaction unit(s) equipped with one or more reactors(s).

The operating conditions used in the hydrocracking processes of the invention may vary widely as a function of the nature of the feed, the quality of the desired products and the facilities available to the refiner. In accordance with the hydrocracking process of the invention, said hydrocracking catalyst is advantageously brought into contact, in the presence of hydrogen, with said hydrocarbon feed at a temperature of more than 200° C., often in the range 250° C. to 480° C., advantageously in the range 320° C. to 450° C., preferably in the range 330° C. to 435° C., at a pressure of more than 1 MPa, often in the range 2 to 25 MPa, preferably in the range 3 to 20 MPa, the space velocity (volume flow rate of feed divided by the volume of catalyst) being in the range 0.1 to 20 $h^{-1}$, preferably in the range 0.1 to 6 $h^{-1}$, still more preferably in the range 0.2 to 3 $h^{-1}$, and the quantity of hydrogen introduced is such that the volume ratio of liters of hydrogen/liters of hydrocarbon is in the range 80 to 5000 L/L, often in the range 100 to 2000 L/L.

These operating conditions used in the hydrocracking process of the invention can generally be used to reach conversions per pass into products with boiling points of at most 370° C. and advantageously at most 340° C., of more than 15%, still more preferably in the range 20% to 95%.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. FR 1353.941, filed Apr. 30, 2013 are incorporated by reference herein.

EXAMPLES

The examples below are presented by way of illustration; they demonstrate the large increase in activity of catalysts prepared in accordance with the process of the invention compared with prior art catalysts, and specify the invention without in any way limiting its scope.

Example 1

W Catalyst Supported on Silica-Alumina, with a Surface Density of 0.3 $W/nm^2$ (in Accordance with the Invention)

The tungsten precursor was dry impregnated in a strictly non-aqueous medium onto a commercial silica-alumina type support (228 $m^2/g$). The support was initially calcined at 300° C. in air for 6 hours at atmospheric pressure. It was then heated to 300° C. for 14 hours under high vacuum ($10^{-5}$ mbar) before being stored in an inert medium, in a glove box. A solution of tungsten (oxo)tetraethoxide, W(=O)(OC$_2$H$_5$)$_4$, was then impregnated onto this support. Dry degassed dichloromethane was used as the solvent. The tungsten precursor was first dissolved in hot solvent, then 0.49 ml of a solution containing 0.033 g of precursor was impregnated onto approximately 0.80 g of dry support. After maturing for 15 hours, the extrudates were dried under vacuum ($10^{-5}$ mbar) for 2 hours at ambient temperature. For this non-sulphurized W/SiAl catalyst, the tungsten content was 1.69% by weight, which corresponded to a surface density of approximately 0.3 $W/nm^2$. This catalyst C1 was in accordance with the invention.

Example 2

W Catalyst Supported on Silica-Alumina, with a Surface Density of 1 $W/Nm^2$ (in Accordance with the Invention)

The tungsten precursor was dry impregnated in a strictly non-aqueous medium onto a commercial silica-alumina type support (228 $m^2/g$). The support was initially calcined at 300° C. in air for 6 hours at atmospheric pressure. It was then heated to 300° C. for 14 hours under high vacuum ($10^{-5}$ mbar) before being stored in an inert medium, in a glove box. A solution of tungsten hexaethoxide, W(OC$_2$H$_5$)$_6$, was then impregnated onto this support. Dry degassed dichloromethane was used as the solvent. The tungsten precursor was first dissolved in hot solvent, then 1.0 ml of a solution containing 0.35 g of precursor was impregnated onto approximately 1.99 g of dry support. After maturing for 15 hours, the extrudates were dried under vacuum ($10^{-5}$ mbar) for 2 hours at ambient temperature. For this non-sulphurized W/SiAl catalyst, the tungsten content was 6.40% by weight, which corresponded to an actual surface density of approximately 1.0 $W/nm^2$. This catalyst C2 was in accordance with the invention.

Example 3

W Catalyst Supported on Silica-Alumina, with a Surface Density of 4 $W/Nm^2$ (in Accordance with the Invention)

The tungsten precursor was dry impregnated in a strictly non-aqueous medium onto a commercial silica-alumina type support (228 $m^2/g$). The support was initially calcined at 300° C. in air for 6 hours at atmospheric pressure. It was then heated to 300° C. for 14 hours under high vacuum ($10^{-5}$ mbar) before being stored in an inert medium, in a glove box. The tungsten precursor was tungsten pentaethoxide, W(OC$_2$H$_5$)$_5$. Dry degassed cyclohexane was used as the solvent. The impregnation solution was prepared from 3.54 g of precursor (approximately 2.30 ml) to which 0.5 ml of cyclohexane was added, then impregnated onto 5.21 g of dry support. The quantity of tungsten was adjusted so as to obtain 4 W/nm$^2$. After maturing for 15 hours, the extrudates were dried under vacuum (10$^{-5}$ mbar) for 2 hours at ambient temperature. For this non-sulphurized W/SiAl catalyst, the tungsten content was 20.48% by weight, which corresponded to an actual surface density of 3.7 W/nm$^2$. This catalyst C3 was in accordance with the invention.

Example 4

W Catalyst Supported on Alumina, with a Surface Density of 4 W/Nm$^2$ (in Accordance with the Invention)

The tungsten was dry impregnated in a strictly non-aqueous medium onto a commercial γ-alumina type support synthesized by calcining a gel of aluminium salts (287 m$^2$/g). The support was initially calcined at 300° C. in air for 6 hours at atmospheric pressure. It was then heated to 300° C. for 14 hours under high vacuum (10$^{-5}$ mbar) before being stored in an inert medium, in a glove box. The tungsten precursor was tungsten pentaethoxide, W(OC$_2$H$_5$)$_5$. The precursor was dissolved in dry degassed cyclohexane then impregnated. The quantity of tungsten was adjusted so as to obtain 4 W/nm$^2$. After maturing for 15 hours, the extrudates were dried under vacuum (10$^{-5}$ mbar) for 2 hours at ambient temperature. For this non-sulphurized W/Al$_2$O$_3$ catalyst, the tungsten content was 25.10% by weight, which corresponded to an actual degree of coverage of 3.8 W/nm$^2$. This catalyst C4 was in accordance with the invention.

Example 5

W Catalyst Supported on Silica-Alumina with a Surface Density of 4 W/Nm$^2$ (not in Accordance with the Invention)

The tungsten was dry impregnated in an aqueous medium onto a commercial silica-alumina type support (228 m$^2$/g). The tungsten precursor was ammonium metatungstate, (NH$_4$)$_6$H$_2$W$_{12}$O$_{40}$.xH$_2$O. The quantity of tungsten was adjusted so as to obtain 4 W/nm$^2$. After maturing for 15 hours, the extrudates were dried at 120° C. for 15 hours. They were then calcined at 450° C. in a stream of air for 2 hours. For this non-sulphurized W/SiAl catalyst, the tungsten content was 19.59% by weight, which corresponded to an actual surface density of 3.5 W/nm$^2$. This catalyst H1 was not in accordance with the invention.

Example 6

W Catalyst Supported on Alumina with a Surface Density of 4 W/Nm$^2$ (not in Accordance with the Invention)

The tungsten was dry impregnated in an aqueous medium onto a commercial γ-alumina type support synthesized by calcining a gel of aluminium salts (289 m$^2$/g). The tungsten precursor was ammonium metatungstate, (NH$_4$)$_6$H$_2$W$_{12}$O$_{40}$.xH$_2$O. The quantity of tungsten was adjusted so as to obtain 4 W/nm$^2$. After maturing for 15 hours, the extrudates were dried at 120° C. for 15 hours. They were then calcined at 450° C. in a stream of air for 2 hours. For this non-sulphurized W/Al$_2$O$_3$ catalyst, the tungsten content was 24.98% by weight, which corresponded to an actual surface density of 3.8 W/nm$^2$. This catalyst H2 was not in accordance with the invention.

Example 7

NiW Catalyst Supported on Silica-Alumina, with a Surface Density of 3 W/Nm$^2$ and Ni/W=0.2 (at/at) (in Accordance with the Invention)

The tungsten was dry impregnated in a strictly non-aqueous medium onto a commercial silica-alumina type support (228 m$^2$/g). The support was initially calcined at 300° C. in air for 6 hours at atmospheric pressure. It was then heated to 300° C. for 14 hours under high vacuum (10$^{-5}$ mbar) before being stored in an inert medium, in a glove box. The tungsten precursor was tungsten pentaethoxide, W(OC$_2$H$_5$)$_5$. Dry degassed cyclohexane was used as the solvent. 1.90 ml of the impregnation solution, prepared from 1.66 g of precursor, was impregnated onto 3.50 g of dry support. The quantity of tungsten was adjusted in order to obtain approximately 3 W/nm$^2$. After maturing for 15 hours, the extrudates were dried under vacuum (10$^{-5}$ mbar) for 2 hours at ambient temperature. This non-sulphurized catalyst was defined by the notation W/SiAl.

A solution of nickel bis-acetylacetonate Ni(acac)$_2$ was then impregnated onto this catalyst. Dry degassed toluene was used as the solvent. The nickel precursor was first dissolved in hot toluene, then 1.5 ml of a solution containing 0.21 g of precursor was impregnated onto approximately 3.50 g of W/SiAl. After maturing for 15 hours, the extrudates were dried under vacuum (10$^{-5}$ mbar) for 3 hours at ambient temperature. For this non-sulphurized NiW/SiAl catalyst, the tungsten and nickel contents were respectively 17.20% and 1.10%, which corresponded to an actual degree of coverage of 3.0 W/nm$^2$ and a NiW atomic ratio of 0.20. This catalyst C5 was in accordance with the invention.

Example 8

NiW Catalyst Supported on Alumina, with a Surface Density of 3 W/Nm$^2$ and Ni/W=0.2 (at/at) (in Accordance with the Invention)

The tungsten was dry impregnated in a strictly non-aqueous medium onto a commercial γ-alumina type support synthesized by calcining a gel of aluminium salts (287 m$^2$/g). The support was initially calcined at 300° C. in air for 6 hours at atmospheric pressure. It was then heated to 300° C. for 14 hours under high vacuum (10$^{-5}$ mbar) before being stored in an inert medium, in a glove box. The tungsten precursor was tungsten pentaethoxide, W(OC$_2$H$_5$)$_5$. Dry degassed cyclohexane was used as the solvent. 2.65 ml of the impregnation solution, prepared from 1.94 g of precursor, was impregnated onto 3.35 g of dry support. The quantity of tungsten was adjusted in order to obtain approximately 3 W/nm$^2$. After maturing for 15 hours, the extrudates were dried under vacuum (10$^{-5}$ mbar) for 2 hours at ambient temperature. This non-sulphurized catalyst was defined by the usual notation W/Al$_2$O$_3$.

A solution of nickel bis-acetylacetonate Ni(acac)$_2$ was then impregnated onto this catalyst. Dry degassed toluene was used as the solvent. The nickel precursor was first dissolved in hot toluene, then 2.10 ml of a solution containing 0.24 g of precursor was impregnated onto approximately 3.30 g of W/Al$_2$O$_3$. After maturing for 15 hours, the extrudates were dried under vacuum ($10^{-5}$ mbar) for 3 hours at ambient temperature. For this non-sulphurized NiW/Al$_2$O$_3$ catalyst, the tungsten and nickel contents were respectively 21.20% by weight and 1.35% by weight, which corresponded to an actual degree of coverage of 3.1 W/nm$^2$ and a NiW atomic ratio of 0.20. This catalyst C6 was in accordance with the invention.

Example 9

NiW Catalyst Supported on Silica-Alumina, with a Surface Density of 3 W/Nm$^2$ (Not in Accordance with the Invention)

The tungsten and the nickel were dry co-impregnated in an aqueous medium onto a commercial silica-alumina type support (228 m$^2$/g). The tungsten precursor was ammonium metatungstate, (NH$_4$)$_6$H$_2$W$_{12}$O$_{40}$.xH$_2$O. The nickel precursor was nickel nitrate, Ni(NO$_3$)$_2$.xH$_2$O. The quantities of the precursors were adjusted so as to obtain 3 W/nm$^2$ and Ni/W=0.20 (at/at). After maturing for 15 hours, the extrudates were dried at 120° C. for 15 hours. They were then calcined at 450° C. in a stream of air for 2 hours. For this non-sulphurized NiW/SiAl catalyst, the quantities of tungsten and nickel were respectively 16.94% by weight and 1.09% by weight, which corresponded to an actual surface density of 3.0 W/nm$^2$ and a NiW atomic ratio of 0.20. This catalyst H3 was not in accordance with the invention.

Example 10

NiW Catalyst Supported on Alumina, with a Surface Density of 3 W/Nm$^2$ (not in Accordance with the Invention)

The tungsten and the nickel were dry co-impregnated in an aqueous medium onto a commercial γ-alumina type support by calcining a gel of aluminium salts (289 m$^2$/g). The tungsten precursor was ammonium metatungstate, (NH$_4$)$_6$H$_2$W$_{12}$O$_{40}$.xH$_2$O. The nickel precursor was nickel nitrate, Ni(NO$_3$)$_2$.xH$_2$O. The quantities of the precursors were adjusted so as to obtain 3 W/nm$^2$ and Ni/W=0.20 (at/at). After maturing for 15 hours, the extrudates were dried at 120° C. for 15 hours. They were then calcined at 450° C. in a stream of air for 2 hours. For this non-sulphurized NiW/Al$_2$O$_3$ catalyst, the quantities of tungsten and nickel were respectively 21.15% by weight and 1.30% by weight, which corresponded to an actual surface density of 3.1 W/nm$^2$ and a NiW atomic ratio of 0.19. This catalyst H4 was not in accordance with the invention.

Example 11

NiWMo Catalyst Supported on Silica-Alumina, with a Surface Density of 3 W/Nm$^2$ and Ni(W+Mo)=0.2 (at/at) (in Accordance with the Invention)

The tungsten was dry impregnated in a strictly non-aqueous medium onto a commercial silica-alumina type support (228 m$^2$/g). The support was initially calcined at 300° C. in air for 6 hours at atmospheric pressure. It was then heated to 300° C. for 14 hours under high vacuum ($10^{-5}$ mbar) before being stored in an inert medium, in a glove box. The tungsten precursor was tungsten pentaethoxide, W(OC$_2$H$_5$)$_5$. Dry degassed cyclohexane was used as the solvent. 2.20 ml of the impregnation solution, prepared from 1.94 g of precursor, was impregnated onto 4.10 g of dry support. The quantity of tungsten was adjusted in order to obtain approximately 3 W/nm$^2$. After maturing for 15 hours, the extrudates were dried under vacuum ($10^{-5}$ mbar) for 2 hours at ambient temperature. This non-sulphurized catalyst was defined by the notation W/SiAl.

Next, a solution of molybdenum pentaethoxide, Mo(OC$_2$H$_5$)$_5$, was impregnated onto this catalyst. Dry degassed dichloromethane was used as the solvent. The molybdenum precursor was dissolved in the hot solvent, then 2.1 ml of a solution containing 0.79 g of precursor was impregnated onto the W/SiAl. After maturing for 15 hours, the extrudates were vacuum dried (5×10$^{-5}$ mbar) for 3 hours at ambient temperature. This non-sulphurized catalyst was defined by the notation WMo/SiAl.

Finally, a solution of nickel bis-acetylacetonate Ni(acac)$_2$ was impregnated onto this catalyst. Dry degassed toluene was used as the solvent. The nickel precursor was first dissolved in hot toluene, then 1.7 ml of a solution containing 0.37 g of precursor was impregnated onto the WMo/SiAl catalyst. After maturing for 15 hours, the extrudates were dried under vacuum (2×10$^4$ mbar) for 5 hours at ambient temperature. For this non-sulphurized NiWMo/SiAl catalyst, the tungsten, molybdenum and nickel contents were respectively 16.32% by weight, 4.21% by weight and 1.49% by weight, which corresponded to an actual surface density of 3.0 W/nm$^2$ and a Ni(W+Mo) atomic ratio of 0.20. This catalyst C7 was in accordance with the invention.

Example 12

Analysis of Sulphurized WS$_2$ Catalysts

The catalysts cited in Examples 3, 4, 5 and 6 were sulphurized ex situ on the sulphurization equipment then analysed by X ray photoelectron spectrometry (XPS) in order to determine the sulphurizability of the deposited W. In the text, the sulphurized samples are given the suffix S. Ex situ sulphurization was carried out in a sulphurization cell. The catalysts were subjected to a stream of sulphurizing gas (H$_2$S/H$_2$ mixture, 15 molar % H$_2$S) at a flow rate of 2 L/h/g$_{catalyst}$ for 2 h at 350° C. The sulphurization cell was then kept at 250° C. and flushed with inert gas (argon) for 2 h. Finally, the sulphurization cell was placed under vacuum ($10^{-1}$ mbar) at a temperature of 120° C. and the catalysts were sealed in ampoules under vacuum and stored in a glove box. For the sulphurized catalysts WS$_2$/SiAl (C3-S, and H1-S) or WS$_2$/Al$_2$O$_3$ (C4-S and H2-S), the quantities of W were approximately identical to those of the non-sulphurized catalysts prepared in Examples 3 to 6.

The W sulphurizability was determined by the relative degree of sulphurization of W observed by XPS. For the analysis, the sulphurized samples were prepared in a glove box to prevent any re-oxidation of the sulphide phase. The sample holder was placed in the analysis chamber under ultra-high vacuum ($10^{-8}$ mbar) and the samples were subjected to a monochromatic X ray beam (Kα line of aluminium, 1486.6 eV). The spectra obtained were then broken down by superimposing several peaks calculated from a shape which was a mixture of a gaussian and a laurentzian form. The quantitative analysis was carried out from the area under the peaks attributed to each of the identified species. In particular, the degree of sulphurization was obtained by analysis of the W 4f contribution of tungsten.

All of the spectra showed the presence of W(IV), attributed to a WS$_2$ phase, W(VI) attributed to the starting oxide, and W(V) attributed to an intermediate phase.

Table 1 only shows the results for the series of catalysts prepared with approximately 4 W/nm².

TABLE 1

Relative degree of sulphurization of tungsten and bond energies determined for the components attributed to WS2 [W(IV)] and to the oxide phase [W(VI)], after calibration with respect to the position of the C 1s peak at 284.6 eV

| Catalyst | % by weight W | Bond energy (eV) for W(VI) | Bond energy (eV) for W(IV) | Relative degree of sulphurization of tungsten (%) |
|---|---|---|---|---|
| C3-S on SiAl (in accordance with the invention) | 20.5 | 36.0 | 32.3 | 80 |
| C4-S on alumina (in accordance with the invention) | 25.1 | 36.0 | 32.2 | 65 |
| H1-S on SiAl (not in accordance with the invention) | 19.6 | 36.0 | 32.3 | 57 |
| H2-S on alumina (not in accordance with the invention) | 25.0 | 35.8 | 32.0 | 48 |

The results show that the catalysts of the invention have degrees of W sulphurization which are substantially higher than the catalysts prepared in a conventional manner from polyoxometallates.

Example 13

Analysis of Sulphurized NiWS Catalysts

The catalysts cited in Examples 7, 8, 9 and 10 were sulphurized ex situ on the sulphurization equipment then analysed by X ray photoelectron spectrometry (XPS) in order to determine the sulphurizability of the deposited W, and the promotion by nickel, of the sulphide phase of the tungsten. In the text, the sulphurized samples are given the suffix —S.

Ex situ sulphurization was carried out in a sulphurization cell. The catalysts were subjected to a stream of sulphurizing gas ($H_2S/H_2$ mixture, 15 molar % $H_2S$) at a flow rate of 2 L/h/$g_{catalyst}$ for 2 h at 350° C. The sulphurization cell was then kept at 250° C. and flushed with inert gas (argon) for 2 h. Finally, the sulphurization cell was placed under vacuum ($10^{-1}$ mbar) at a temperature of 120° C. and the catalysts were sealed in ampoules under vacuum and stored in a glove box. For the sulphurized catalysts $NiWS_2/SiAl$ (C5-S, and H3-S) or $NiWS_2/Al_2O_3$ (C6-S and H4-S), the W contents were approximately identical to those of the non-sulphurized catalysts prepared in Examples 7 to 10.

The sulphurizability of W was determined by the relative degree of sulphurization of W observed by XPS, as described in Example 12. All of the W 4f spectra showed the presence of W(IV) attributed to a $WS_2$ phase, W(VI) attributed to the starting oxide, as well as W(V) attributed to an intermediate phase. The Ni 2p spectra showed the presence of a promoted phase, NiWS, of a phase competing with the sulphurization, NiS, and a nickel phase bonded to the support.

TABLE 2

Relative degree of sulphurization of tungsten, and bond energies (B.E.) determined for the components attributed to WS2 [W(IV)], to the oxide phase [W(VI)] and to the promoted phase NiWS, after calibration with respect to the position of the C 1s peak at 284.6 eV

| Catalyst | % by weight W | B.E. (eV) for W(VI) | B.E. (eV) for W(IV) | B.E. (eV) for the NiWS contribution | Relative degree of sulphurization of tungsten (%) |
|---|---|---|---|---|---|
| C5-S on SiAl (in accordance with the invention) | 17.2 | 35.8 | 32.2 | 853.7 | 76 |
| C6-S on alumina (in accordance with the invention) | 21.2 | 36.0 | 32.2 | 853.6 | 62 |
| H3-S on SiAl (not in accordance with the invention) | 16.9 | 36.1 | 32.1 | 853.5 | 60 |
| H4-S on alumina (not in accordance with the invention) | 21.2 | 35.9 | 32.1 | 853.5 | 50 |

The results show that the catalysts of the invention have degrees of tungsten sulphurization which are substantially higher than the catalysts prepared in a conventional manner from polyoxometallates.

Example 14

Test for the Hydrogenation of Toluene (Aromatic Model Molecule) in the Presence of Aniline The test for the hydrogenation of toluene in the presence of aniline is intended to evaluate the hydrogenating activity of supported or bulk sulphurized catalysts in the presence of $H_2S$ and under hydrogen pressure. The isomerization which characterizes the acid function of the catalyst is inhibited by the presence of aniline, at low temperatures and/or by the presence of $NH_3$ (obtained from the decomposition of aniline) at higher temperatures. The aniline and/or $NH_3$ will react with the acidic sites of the support by an acid-base reaction. The characteristic isomerization reactions of the acidity of the support then do not exist.

We were careful to carry out the comparison of the catalysts on the same catalytic test unit in order not to falsify the comparisons by using different catalytic test tools which could produce out-of-line results.

The catalytic test was carried out in the gas phase in a fixed bed traversed reactor. The test can be broken down into two distinct phases, sulphurization and the catalytic test. The test was carried out at 60 bar.

The catalysts were initially sulphurized ex situ in the gas phase (($H_2S/H_2$ mixture) in which the quantity of $H_2S$ was 15% by volume) at a temperature of 350° C. for 2 h.

Activation Phase:

The catalysts were subjected to a rise in temperature under test charge in a fixed bed traversed tube reactor of a Flowrence type pilot unit (from Avantium), the fluids moving from top to bottom. The measurements of the hydrogenating activity were carried out immediately after reaching the test temperature.

Catalytic Test:

The test feed was composed of dimethyldisulphide (DMDS), toluene, cyclohexane and aniline.

The stabilized catalytic activities of equal volumes of catalysts (450 μL) were measured at a temperature of 350° C.

The operating conditions of the test were as follows (assuming total vaporization and the perfect gas law):

For Ptot=60 bar and T=350° C.:

$PpH_2$=36.62 bar $PpNH_3$=0.09 bar $PpH_2S$=2.16 bar

Pptoluene=3.75 bar

Ppcyclohexane=15.22 bar

HSV=4 L/L/h during the activation phase, and HSV=2 L/L/h and $H_2$/feed=450 L/L during the test phase.

Effluent samples were analysed by gas phase chromatography. The catalytic performances of the catalysts are expressed using the corresponding hydrogenating activity, using first order kinetics:

$$AH_{1,order} = \ln\frac{100}{(100 - \% \ HYD_{toluene})}$$

% $HYD_{toluene}$ corresponds to the percentage of hydrogenated toluene.

The catalytic performances are shown in Tables 3 to 6.

TABLE 3

Relative hydrogenating activity of catalysts C3 and H1 on silica-alumina These are expressed as the relative activity, taking that of catalyst H1 to be equal to 100.

| Catalyst | Hydrogenating activity relative to H1 |
|---|---|
| C3 (in accordance with the invention) | 182 |
| H1 (not in accordance with the invention) | 100 |

TABLE 4

Relative hydrogenating activity of catalysts C4 and H2 on alumina These are expressed as the relative activity, taking that of catalyst H1 to be equal to 100.

| Catalyst | Hydrogenating activity relative to H2 |
|---|---|
| C4 (in accordance with the invention) | 167 |
| H2 (not in accordance with the invention) | 100 |

Tables 3 and 4 show the large gain in hydrogenating power obtained for the catalysts claimed in accordance with the invention prepared on silica-alumina (C3) and on alumina (C4). Catalysts C3 and C4, prepared from the cited tungsten precursor of the invention are more active than the catalysts which are homologous in formulation but prepared by conventional pathways using heteropolyanion salts (H1 and H2).

TABLE 5

Relative hydrogenating activity of NiW catalysts C5 and H3 on silica-alumina These are expressed as the relative activity, taking that of catalyst H3 to be equal to 100.

| Catalyst | Hydrogenating activity relative to H3 |
|---|---|
| C5 (in accordance with the invention) | 175 |
| H3 (not in accordance with the invention) | 100 |

TABLE 6

Relative hydrogenating activity of NiW catalysts C6 and H4 on alumina These are expressed as the relative activity, taking that of catalyst H4 to be equal to 100.

| Catalyst | Hydrogenating activity relative to H4 |
|---|---|
| C6 (in accordance with the invention) | 168 |
| H4 (not in accordance with the invention) | 100 |

Tables 5 and 6 show the large gain in hydrogenating power obtained for the catalysts claimed in accordance with the invention prepared on silica-alumina (C5) and on alumina (C6). Catalysts C5 and C6, prepared from the tungsten and nickel precursors of the invention, are more active than the catalysts which are homologous in formulation but prepared by conventional pathways using heteropolyanion salts (H3 and H4).

Example 15

Degree of Sulphurization of Catalysts Promoted with Nickel, Based on W and Sulphurized at 623K

| Catalyst | % by weight W | Relative % of $WS_2$ evaluated by XPS | Relative % of NiWS promoted phase |
|---|---|---|---|
| C5-S on SiAl (in accordance with the invention) | 17.2 | 76 | 65 |
| H3-S on SiAl (not in accordance with the invention) | 16.9 | 60 | 50 |

-continued

| Catalyst | % by weight W | Relative % of $WS_2$ evaluated by XPS | Relative % of NiWS promoted phase |
|---|---|---|---|
| C6-S on alumina (in accordance with the invention) | 21.2 | 45 | 50 |
| H4-S on alumina (not in accordance with the invention) | 21.2 | 35 | 42 |

The results show that the high activities obtained for the NiW catalysts C5 and C6 are at least partly due to their better sulphurization and their better promotion compared with the catalysts prepared in a more conventional manner using preparations involving heteropolyanion salts.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for the preparation of a catalyst comprising at least one support, optionally at least one metal from group VIII of the periodic classification of the elements and at least tungsten, said process comprising:

introducing tungsten onto at least one support, in an organic solvent A, in the form of at least one mononuclear precursor compound based on W, in its monomeric or dimeric form, having at least one W=O or W—OR bond or at least one W=S or W—SR bond, where $R=C_xH_y$, $x \geq 1$, and $(x-1) \leq y \leq (2x+1)$, or $R=Si(OR')_3$ or $R=Si(R')_3$, $R'=C_xH_{y'}$, $x' \geq 1$, and $(x'-1) \leq y' \leq (2x'+1)$, and comprising at least one final step for gas phase sulphurization, in situ and/or ex situ.

2. The process as claimed in claim 1, in which the metal from group VIII is cobalt, iron or nickel.

3. The process as claimed in claim 2, in which the metal from group VIII is nickel.

4. The process as claimed in claim 1, in which the tungsten precursor is a mononuclear precursor based on tungsten W, in its monomeric or dimeric form, with formula $W(=O)_n(=S)_{n'}(OR)_a(SR')_b(L1)_c(L2)_d(L3)_e(L4)_f(L5)_g$, where $R=C_xH_y$, $x \geq 1$, and $(x-1) \leq y \leq (2x+1)$, or $R=Si(OR'')_3$ or $R=Si(R'')_3$, $R''=C_{x''}H_{y''}$, $x'' \geq 1$, and $(x''-1) \leq y'' \leq (2x''+1)$, $R'=C_{x'}H_{y'}$, $x' \geq 1$, and $(x'-1) \leq y' \leq (2x'+1)$, or $R'=Si(OR''')_3$ or $R'=Si(R''')_3$, $R'''=C_{x'''}H_{y'''}$, $x''' \geq 1$, and $(x'''-1) \leq y''' \leq (2x'''+1)$, $0 \leq n+n' \leq 2$, $0 \leq n \leq 2$, and $0 \leq n' \leq 2$, if $n=n'=0$, then $a \neq 0$ or $b \neq 0$, and $a+b+c+d+e+f+g=6$ and $0 \leq a \leq 6$, $0 \leq b \leq 6$, $0 \leq c \leq 6$, $0 \leq d \leq 6$, $0 \leq e \leq 6$, $0 \leq f \leq 6$, $0 \leq g \leq 6$;

or $a+b+c+d+e+f+g=5$ and $0 \leq a \leq 5$, $0 \leq b \leq 5$, $0 \leq c \leq 5$, $0 \leq d \leq 5$, $0 \leq e \leq 5$, $0 \leq f \leq 5$, $0 \leq g \leq 5$;

or $a+b+c+d+e+f+g=4$ and $0 \leq a \leq 4$, $0 \leq b \leq 4$, $0 \leq c \leq 4$, $0 \leq d \leq 4$, $0 \leq e \leq 4$, $0 \leq f \leq 4$, $0 \leq g \leq 4$;

if ($n=1$ and $n'=0$) or ($n'=1$ and $n=0$), then $a+b+c+d+e+f+g=4$ and $0 \leq a \leq 4$, $0 \leq b \leq 4$, $0 \leq c \leq 4$, $0 \leq d \leq 4$, $0 \leq e \leq 4$, $0 \leq f \leq 4$, $0 \leq g \leq 4$;

or $a+b+c+d+e+f+g=3$ and $0 \leq a \leq 3$, $0 \leq b \leq 3$, $0 \leq c \leq 3$, $0 \leq d \leq 3$, $0 \leq e \leq 3$, $0 \leq f \leq 3$, $0 \leq g \leq 3$;

if $n+n'=2$ and $0 \leq n \leq 2$ and $0 \leq n' \leq 2$, then $a+b+c+d+e+f+g=2$ and $0 \leq a \leq 2$, $0 \leq b \leq 2$, $0 \leq c \leq 2$, $0 \leq d \leq 2$, $0 \leq e \leq 2$, $0 \leq f \leq 2$, $0 \leq g \leq 2$;

and (L1), (L2), (L3), (L4) and (L5) are selected from the group consisting of ligands of the type THF, dimethyl ether, dimethylsulphide, $P(CH_3)_3$, allyl, aryl, halogen, amine, acetate, acetylacetonate, halide, hydroxide and —SH.

5. The process as claimed in claim 4, in which the precursor is $W(OEt)_5$, $W(OEt)_6$, $W(=O)(OEt)_4$, $W(=S)(OEt)_4$, $W(=S)(SEt)_4$, $W(=O)_2(OEt)_2$, $W(OC_6H_5)_6$, $W(SEt)_5$, $W(SEt)_6$, $W(OEt)_3(SEt)_2$, $W(OEt)_4(SEt)$, or $W(=O)(OEt)_3(acac)$ with Et=$CH_2CH_3$ (ethyl group) and acac=$(CH_3COCHCOCH_3)^-$ (acetylacetonate), in their monomeric or dimeric form.

6. The process as claimed in claim 1, in which molybdenum is also introduced into the catalyst, in the form of a precursor in an aqueous, alcoholic or organic solvent.

7. The process as claimed in claim 6, in which the molybdenum precursor is a mononuclear precursor, in its monomeric or dimeric form, comprising at least one Mo=O or Mo—OR bond or at least one Mo=S or Mo—SR bond where $R=C_xH_y$, $x \geq 1$, and $(x-1) \leq y \leq (2x+1)$, or $R=Si(OR')_3$ or $R=Si(R')_3$, $R'=C_xH_{y'}$, $x' \geq 1$, and $(x'-1) \leq y' \leq (2x'+1)$.

8. The process as claimed in claim 7, in which the molybdenum precursor is a compound with the following formula $Mo(=O)_n(=S)_{n'}(OR)_a(SR')_b(L1)_c(L2)_d(L3)_e(L4)_f(L5)_g$, where
R=C$_x$H$_y$,
x≥1, and
(x−1)≤y≤(2x+1),
or
R=Si(OR")$_3$ or R=Si(R")$_3$,
R"=C$_{x"}$H$_{y"}$,
x"≥1, and
(x"−1)≤y"≤(2x"+1),
R'=C$_{x'}$H$_{y'}$,
x'≥1, and
(x'−1)≤y'≤(2x'+1),
or
R'=Si(OR'")$_3$ or R'=Si(R'")$_3$,
R'"=C$_{x'"}$H$_{y'"}$,
x'"≥1, and
(x'"−1)≤y'"≤(2x'"+1),
0≤n+n'≤2,
0≤n≤2, and
0≤n'≤2,
if n=n'=0,
then
a≠0 or b≠0
and
a+b+c+d+e+f+g=6 and 0≤a≤6, 0≤b≤6, 0≤c≤6, 0≤d≤6, 0≤e≤6, 0≤f≤6, 0≤g≤6;
or
a+b+c+d+e+f+g=5 and 0≤a≤5, 0≤b≤5, 0≤c≤5, 0≤d≤5, 0≤e≤5, 0≤f≤5, 0≤g≤5;
or a+b+c+d+e+f+g=4 and 0≤a≤4, 0≤b≤4, 0≤c≤4, 0≤d≤4, 0≤e≤4, 0≤f≤4, 0≤g≤4;
if (n=1 and n'=0) or (n'=1 and n=0),
then
a+b+c+d+e+f+g=4 and 0≤a≤4, 0≤b≤4, 0≤c≤4, 0≤d≤4, 0≤e≤4, 0≤f≤4, 0≤g≤4;
or
(a+b+c+d+e+f+g=3 and 0≤a≤3, 0≤b≤3, 0≤c≤3, 0≤d≤3, 0≤e≤3, 0≤f≤3, 0≤g≤3;
if n+n'=2 and 0≤n≤2 and 0≤n'≤2,
then
a+b+c+d+e+f+g=2 and 0≤a≤2, 0≤b≤2, 0≤c≤2, 0≤d≤2, 0≤e≤2, 0≤f≤2, 0≤g≤2;
and
(L1), (L2), (L3), (L4) and (L5) are selected from the group consisting of ligands of the type THF, dimethyl ether, dimethylsulphide, P(CH$_3$)$_3$, allyl, aryl, halogen, amine, acetate, acetylacetonate, halide, hydroxide and —SH.

9. The process as claimed in claim 8, in which the molybdenum precursor is Mo(OEt)$_5$.

10. The process for the preparation of a catalyst as claimed in claim 1, in which the tungsten, optionally the molybdenum, optionally the metal or metals from group VIII, are introduced simultaneously or in succession.

11. The process for the preparation of a catalyst as claimed in claim 1, comprising at least one final step for gas phase sulphurization, in situ.

12. The process for the preparation of a catalyst as claimed in claim 1, comprising at least the following steps:
a) impregnation by bringing a solution S comprising the organic solvent A with at least said mononuclear precursor based on tungsten, in its monomeric or dimeric form, having at least one W=O or W—OR bond or at least one W=S or W—SR bond,
where
R=C$_x$H$_y$,
x≥1, and
(x−1)≤y≤(2x+1),
or
R=Si(OR')$_3$ or R=Si(R')$_3$,
R'=C$_x$H$_y$,
x'≥1, and
(x'−1)≤y'≤(2x'+1),
into contact with a porous mineral support, which has been calcined under vacuum or in a stream of inert gas;
b) maturing in an anhydrous atmosphere;
c) drying the impregnated support in an anhydrous atmosphere or under vacuum or in a stream of inert gas; and
d) ex situ sulphurization in a H$_2$S/H$_2$ or H$_2$S/N$_2$ mixture containing at least 5% by volume of H$_2$S in the mixture at a temperature equal to or higher than ambient temperature.

13. The process for the preparation of a catalyst as claimed in claim 12, in which the optional molybdenum precursor is introduced into the impregnation step a) in the same solution S as the tungsten precursor.

14. The process for the preparation of a catalyst as claimed in claim 12, in which the optional molybdenum precursor is introduced in a post-impregnation step a2) after drying at c).

15. The process for the preparation of a catalyst as claimed in claim 12, in which the optional metal from group VIII is introduced into step a) in the same solution S as the tungsten precursor or after the drying c) in a post-impregnation step a2) with the aid of a solution containing an organic solvent B, or after the sulphurization step d) in a post-impregnation step a3) with the aid of an aqueous or organic solution.

16. The process for the preparation of a catalyst as claimed in claim 1, comprising at least one final step for gas phase sulphurization, ex situ.

17. A catalyst which has been prepared as claimed in claim 1.

18. The catalyst as claimed in claim 17, comprising a cumulative quantity of (tungsten+molybdenum) in the range of 4% to 30% by weight and a metal or metals from group VIII content in the range of 0.1% to 8% by weight with respect to the total catalyst weight.

19. The process for the hydrogenation of a hydrocarbon feed, comprising subjecting said feed to hydrogenation conditions in the presence of a catalyst according to claim 17.

20. The process as claimed in claim 19, comprising hydrotreatment or hydrocracking.

* * * * *